United States Patent [19]
Yurino et al.

[11] Patent Number: 6,127,125
[45] Date of Patent: Oct. 3, 2000

[54] SAMPLE APPLICATION METHOD AND DEVICE

[75] Inventors: Noriko Yurino; Kenji Yamamoto; Hisanori Nasu, all of Kanagawa, Japan

[73] Assignee: Hitachi Software Engineering Co., Ltd., Japan

[21] Appl. No.: 09/264,463

[22] Filed: Mar. 8, 1999

[30] Foreign Application Priority Data

Mar. 30, 1998 [JP] Japan .................................... 10-084639

[51] Int. Cl.[7] .................................................. C12Q 1/68
[52] U.S. Cl. ........................ 435/6; 435/810; 436/501; 536/25.3; 536/23.1; 935/77; 935/78; 935/88
[58] Field of Search ........................ 435/6, 810; 436/501; 536/25.3, 23.1; 935/77, 78, 88

[56] References Cited

U.S. PATENT DOCUMENTS 5,849,486  12/1998  Heller et al. ................................ 435/6

*Primary Examiner*—Kenneth R. Horlick
*Assistant Examiner*—Janell E. Taylor
*Attorney, Agent, or Firm*—Fish & Richardson P.C.

[57] ABSTRACT

A sample application method including the steps of: rotating a biochip including a plurality of regions bound with various probes; and dropping a sample onto generally a center of rotation of the rotating biochip so as to apply the sample to the plurality of regions.

4 Claims, 8 Drawing Sheets

SAMPLE APPLICATION METHOD AND DEVICE

FIELD OF THE INVENTION

The present invention relates to a method and a device for applying a sample to probe DNA or the like bound to a biochip for the purpose of DNA analysis or the like.

BACKGROUND OF THE INVENTION

In the fields of molecular biology and biochemistry, biopolymers such as nucleic acids and proteins from organisms are identified and fractionated in order to search useful genes or to diagnose diseases. As a pre-treatment of such identification and fractionation, a hybridization reaction is often employed in which a target molecule in a sample is hybridized with a nucleic acid or a protein of a known sequence. However, when this method is employed for analyzing a hereditary disease, for example, it is troublesome and time-consuming to identify the disease since about 3,000 hereditary diseases are currently known. The currently proceeding human genome projects aim at analyzing all of human genomes which presumably total several hundred thousands of bases. Obviously, it is very time-consuming and troublesome if this is to be conducted completely in manual.

On the other hand, devices have been developed which are capable of processing a mass of sample in a short time. One example of such device is described in "Rapid genetic sequence analysis using a DNA probe array system: Thane Kreiner, Affimetrix, Inc., (American Laboratory, 1996 March, pp.39–43)". This analyzer uses a biochip 100 shown in FIG. 10 which is provided with a plurality of features 101 arranged in matrix on the surface thereof. The features 101 are immobilized with various kinds of probes. The biochip 100 is placed in a reaction vessel called a chamber together with sample DNA such that the sample DNA labeled with fluorescence hybridizes with the probes bound to the features 101 of the biochip 100. Then, the biochip 100 is irradiated with excitation light, thereby detecting a fluorescence intensity at each feature 101 to determine an amount of binding between each probe and the sample DNA. The result can be used as advantageous information.

In the case of the above-described device, the biochip 100 bound with probes is placed in the reaction vessel. The sample DNA or other reagent in a sample or a reagent container is injected into the reaction vessel through a tube by a peristaltic pump, whereby the biochip 100 is partially immersed in the sample or the reagent injected into the reaction vessel. The sample DNA or the reagent in the reaction vessel is spread or applied to the entire features 101 by shaking the reaction vessel.

However, the above-described way of applying the sample to all of the probe-bound features 101 of the biochip 100 requires a large amount of sample. For example, in the case of a biochip with an area of 1.28 cm×1.28 cm (i.e., 1.64 cm$^2$), the chamber needs to be filled with a sample of 350 $\mu$l to perform a single hybridization reaction. Considering the fact that the sample from the sample container is introduced into the reaction vessel via the tube, the actual amount of the sample required will increase by several times. In addition, there is also a need of washing an excessive amount of the sample away. Reaction errors caused by varying amounts of sample applications among the features 101 have been responsible for low reliability of the reaction vessel. In order to prevent such errors, an even amount of the sample needs to be applied to the entire features 101.

The present invention was accomplished in view of the above prior art problems, and aims at providing a sample application method and device wherein a sample is evenly applied over entire features of a biochip with a less amount of the sample.

The term "sample" as used with the present invention, refers not only to a sample collected from an analyte but also to various reagents. Specifically, the term "sample" as used herein includes any fluids applied to the features of the biochip, such as a buffer solution containing sample DNA or a reagent used for PCR (Polymerase Chain Reaction).

SUMMARY OF THE INVENTION

According to the present invention, the above-described aim is accomplished by rotating a biochip bound with probes and dropping a sample onto generally the center of rotation, i.e., the center or the vicinity of the center of rotation, of the rotating biochip. The sample that is dropped onto generally the center of rotation of the rotating biochip spreads toward the periphery of the biochip due to the centrifugal force, to be evenly applied to the entire features of the biochip. In order to evenly spread a small amount of sample over the entire features, the surface of the biochip needs to be in a state where the sample can easily spread. For this purpose, a thin layer of a buffer (for example, Tris-HCl buffer) is preferably applied to the surface of the biochip in advance.

Thus, a sample application method of the present invention includes the steps of: rotating a biochip including a plurality of regions (i.e., features) bound with various probes; and dropping a sample onto generally a center of rotation of the rotating biochip so as to apply the sample to the plurality of regions. The biochip may be circular, quadrature, or any other shape.

Furthermore, the sample application method of the present invention includes the steps of: moistening with a buffer a surface of a biochip including a plurality of regions (i.e., features) bound with various probes; and dropping a sample onto generally a center of rotation of the rotating biochip so as to apply the sample to the plurality of regions. As the buffer, Tris-HCl buffer (NaCl, Tris-HCl (pH 8.0), EDTA (ethylenediaminetetraacetic acid), SDS (sodium dodecyl sulfate)), or the like may be used. By moistening the surface of the biochip with the buffer prior to the application of the sample, a minute amount of sample can be easily and evenly applied to all of the probe-bound regions while preventing evaporation of the sample.

A sample application method of the present invention includes the steps of: rotating a biochip including a plurality of regions (i.e., features) bound with various probes; dropping a buffer onto generally a center of rotation of the rotating biochip to moisten the surface of the biochip with the buffer; and dropping a sample onto generally the center of rotation of the rotating biochip so as to apply the sample to the plurality of regions. By dropping the buffer onto generally the center of rotation of the rotating biochip, an extremely thin layer of buffer can be formed on the surface of the biochip. Thus, when a minute amount of sample is applied thereto under a centrifugation condition, the entire probe-bound regions can be covered with the sample while preventing evaporation of the sample.

According to a sample application method of the present invention, a plurality of sample drops may be applied to generally the center of rotation of the rotating biochip. The plurality of minute drops may be applied simultaneously or successively. In order to prevent evaporation of the moisture of the sample on the rotating biochip, the humidity of the atmosphere for applying the sample is kept as high as possible, preferably at a relative humidity of 95% or higher.

According to one aspect, the sample may be a biopolymer such as a nucleic acid or a protein which selectively hybridizes with the probes. In the case where the sample is a nucleic acid, it is preferable in hybridizing the sample and the probe, that the temperature of the biochip is initially set at 90–100° C. and then gradually cooled down to room temperature. The temperature of the biochip may be set at 90–100° C. before or after the sample application. In the latter case, the sample is dropped onto the biochip at room temperature and then the temperature thereof may be increased. The sample may be, for example, human genome DNA, in which case the sample is applied to the features of the biochip to perform PCR. In the case where the sample is a protein which selectively hybridizes with the probe, the sample and the probe are bound to each other while maintaining the temperature of the biochip at 30–40° C.

A sample application device of the present invention includes: a biochip supporting member for supporting a biochip including a plurality of regions (i.e., features) bound with various probes; a driver for rotating the biochip supporting member; and a sample injection member for dropping the sample onto generally a center of rotation of the biochip.

A sample application device of the present invention includes: a biochip supporting member for supporting a biochip including a plurality of regions (i.e., features) bound with various probes; a driver for rotating the biochip supporting member; a buffer injection member for dropping a buffer onto generally a center of rotation of the biochip; and a sample injection member for dropping a sample onto generally the center of rotation of the biochip. By moistening the surface of the biochip with the buffer prior to the application of the sample, a minute amount of sample can be easily and evenly applied to the entire probe-bound regions.

A sample application device may be provided with: a humidifier for keeping the ambient atmosphere around the biochip at a high humidity so as to prevent the applied sample on the surface of the rotating biochip from drying; and a temperature controller for controlling the temperature of the biochip. Moreover, the sample injection member may be used to apply a plurality of sample drops to generally the center of rotation of the biochip. The optimum rotational speed of the biochip may suitably be set in accordance with a viscosity and an amount of the applied sample.

According to the present invention, an minute amount of sample is applied to a rotating biochip so that it is evenly spread over the entire features of the biochip by the centrifugal force caused by the rotation. As a result, unevenness of application can be avoided even with a small amount of sample, thereby saving an amount of sample and enhancing the accuracy of the analysis. In the case where the biochip is a disk with a diameter of 2 cm for instance, an amount of sample required for an even application over the entire features of the biochip is as less as 50–100 μl.

DETAILED DESCRIPTION OF THE INVENTION

Hereinafter, the present invention will be described in more detail by way of examples with reference to the accompanying drawings.

Figure 1:
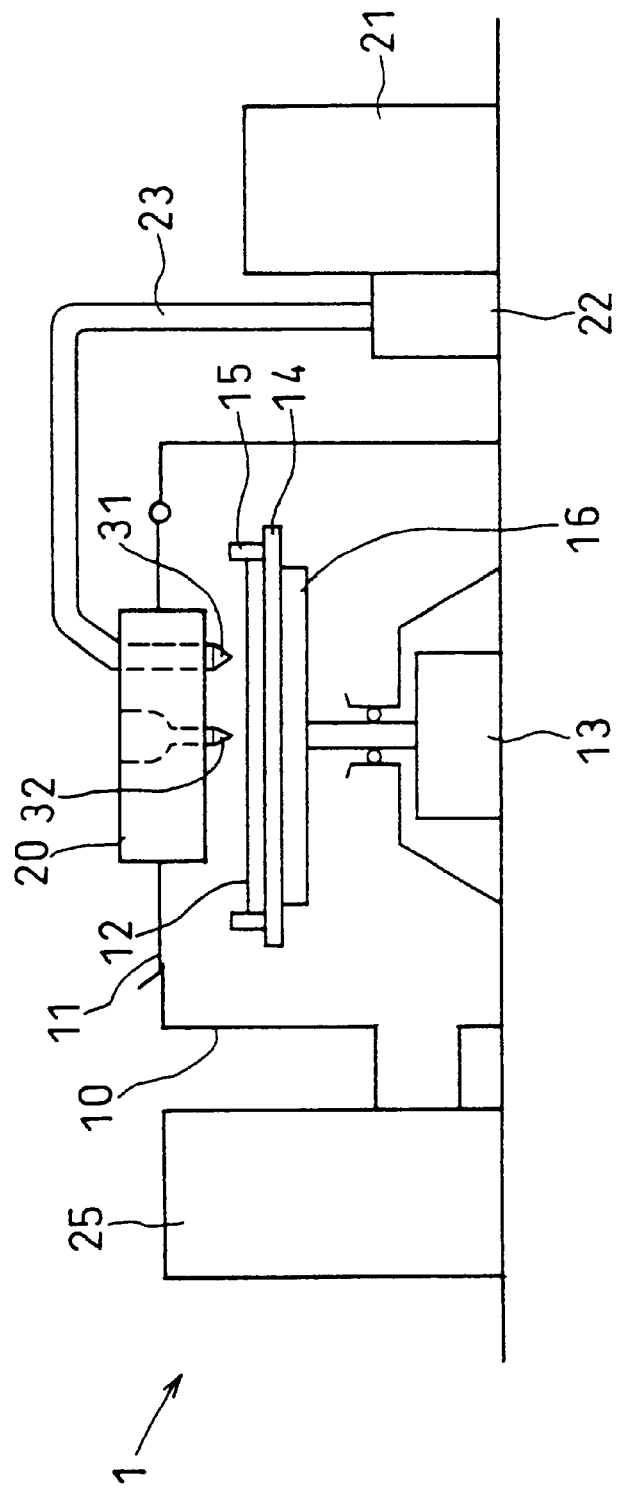
FIG. 1 is a schematic cross-sectional view showing one example of sample application device according to the present invention.

FIG. 1 is a schematic cross-sectional view showing an exemplary sample application device 1 according to the present invention. The sample application device 1 includes a body 10 provided with an openable lid 11, a mechanism for rotating a biochip 12 in the body 10, a rotative head 20 for dropping a buffer or a sample onto a center of rotation of the rotating biochip 12, a humidifier 25 for keeping the atmosphere inside the body 10 at a high humidity, and the like. The biochip 12 is fixed on a rotative plate 14 with a plurality of fixing pins 15 located tangential to the circumference of the biochip 12. The rotative plate 14 is rotated by a motor 13. The rotative plate 14 is also provided with a temperature controller 16 such as a heater which controls the temperature of the rotative plate 14 as well as the temperature of the biochip 12 to be at a predetermined temperature. The humidifier 25 may be a supersonic humidifier or the like, which deliver steam to keep a relative humidity inside the body 10 at 95% or higher.

Figure 2:
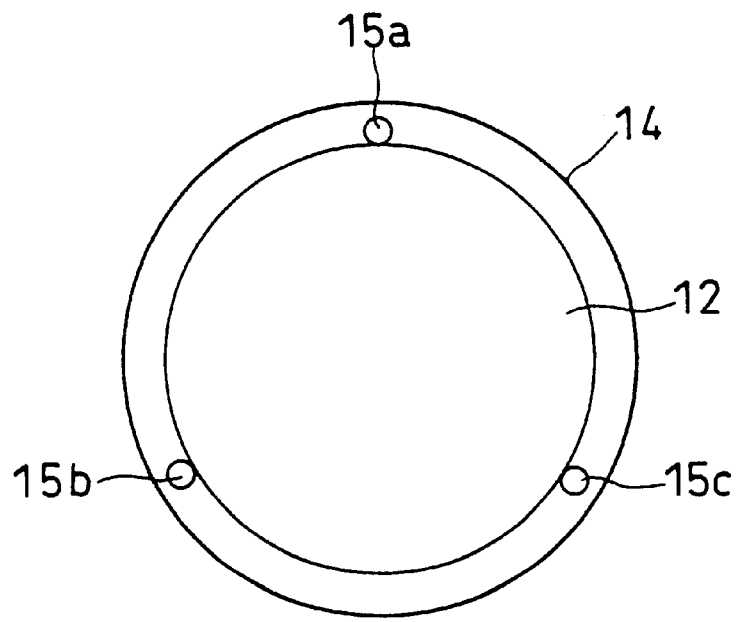
FIG. 2 is a plan view of a rotative plate carrying a biochip.
Figure 3:
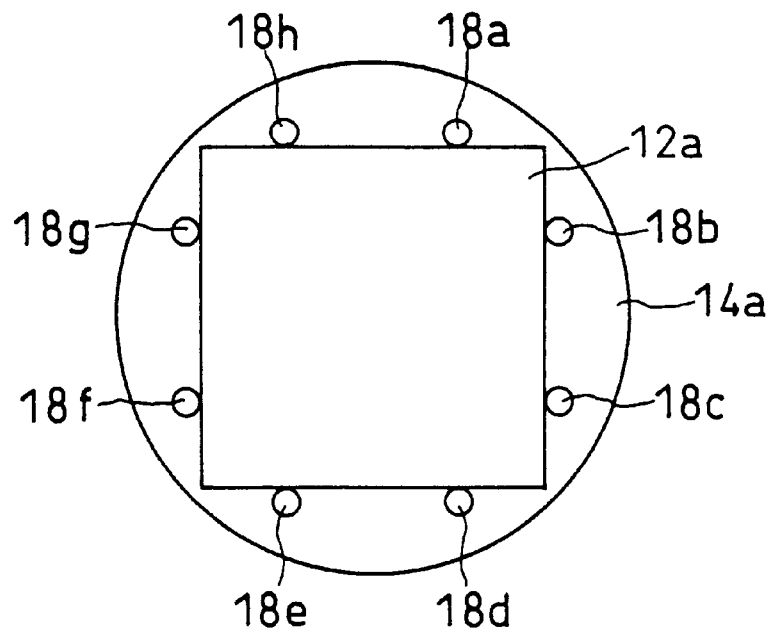
FIG. 3 is a plan view of a rotative plate carrying a quadrilateral biochip.

FIG. 2 is a plan view of the rotative plate 14 carrying the biochip 12. The biochip 12 has a plurality of features bound with probes on the surface thereof, and is fixed on the rotative plate 14 with the pins 15a to 15c tangential to the circumference of the biochip 12. Although elements for fixing the biochip 12 illustrated herein are pins, a chuck, vacuum adsorption, a fixing tooth, or any kind of element may also be used as long as it enables the biochip 12 to rotate together with the rotation plate 14 while keeping the center of rotation stationary. Furthermore, although the biochip 12 shown in FIG. 2 is circular, the biochip is not limited thereto. FIG. 3 is a plan view of a rotative plate 14a carrying a quadrilateral biochip 12a. The quadrilateral biochip 12a is fixed on the rotative plate 14a with fixing pins 18a to 18h, or the like.

Returning to FIG. 1, the rotative head 20 is rotatably attached to the lid 11 of the body 10 and is provided with a buffer nozzle 31 and a sample nozzle 32 for dropping a buffer and a sample, respectively, onto or onto the vicinity of the center of rotation. The buffer is supplied from a buffer container 21 to the buffer nozzle 31 through a tube 23 by a pump 22.

Figure 4:
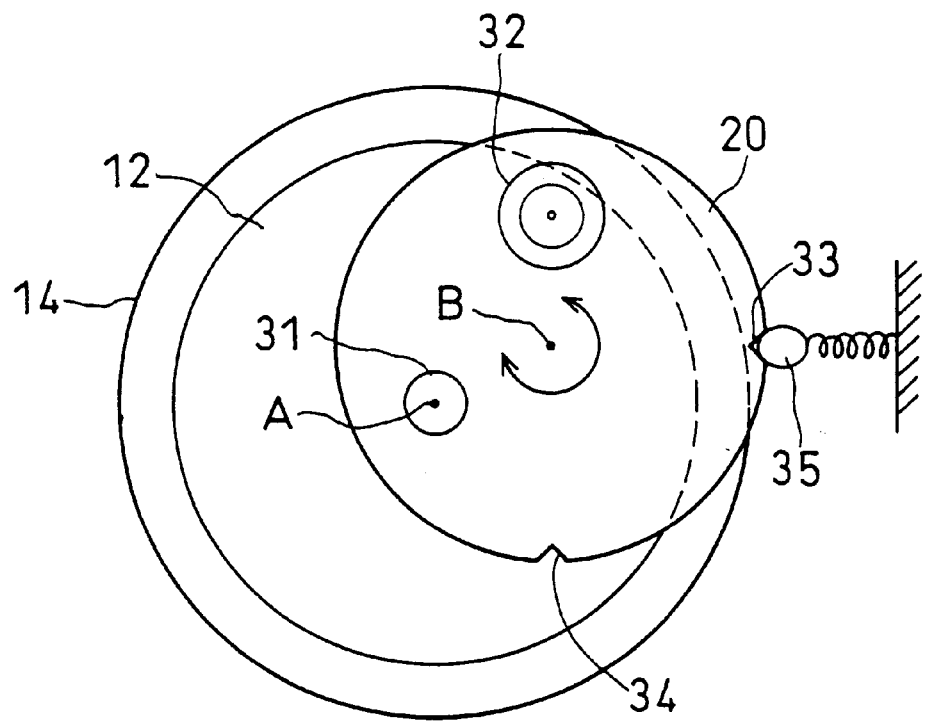
FIG. 4 is a schematic view for illustrating a positional relationship between a rotative head and the biochip fixed on the rotative plate.

FIG. 4 is a schematic view for illustrating a positional relationship between the rotative head 20 and the biochip 12 fixed on the rotative plate 14. By turning the rotative head 20 with respect to the rotational axis B, the buffer nozzle 31 and the sample nozzle 32 may be selectively positioned above the center of rotation A of the rotative plate 14. The rotative head 20 is driven preferably with a driver, e.g., a motor, to position the nozzles 31 and 32 above the center of rotation A. Alternatively, the rotative head 20 may be turned manually, in which case notches 33 and 34 are provided at the peripheral portion of the rotative head 20 such that a movable protrusion 35 which is elastically supported by the lid 11 (FIG. 1) engages with the notches 33 and 34, thereby regulating and securing the position of the rotative head 20.

Figure 5:
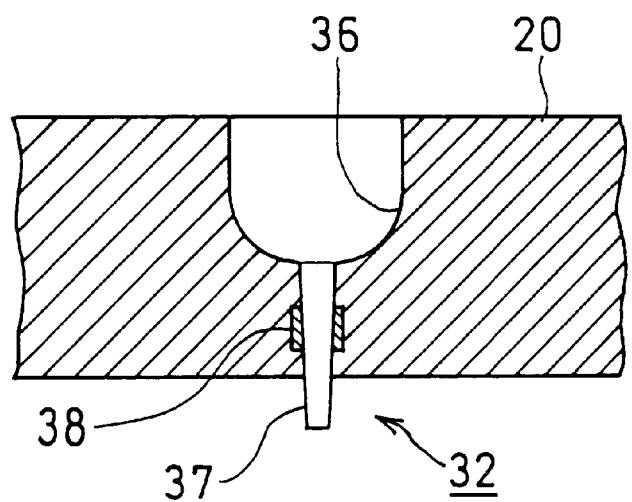
FIG. 5 is a cross-sectional view showing an example of a sample nozzle provided in the rotative head.

FIG. 5 is a cross-sectional view showing an example of the sample nozzle 32 held by the rotative head 20. The sample nozzle 32 includes a sample injection opening 36 with a relatively large aperture diameter, and a nozzle portion 37 with a narrow aperture diameter communicating with the sample injection opening 36. A heater 38 is provided in contact with a part of the nozzle portion 37. When a pulsed current is passed to the heater 38 where a sample is present in the sample nozzle 32, the temperature of the heater 38 is increased and a bubble is generated in the sample at the nozzle portion 37. The bubble pushes a drop of the sample out from a tip of the nozzle 32 towards the center of rotation A of the biochip 12. The amount of the sample drop leaving the tip of the nozzle 32 may be controlled by the current passed to the heater 38. Moreover, by passing a plurality of pulsed currents to the heater 38, a plurality of sample drops may be successively applied to the center of rotation A of the biochip 12. Alternatively, the same effect can be obtained by providing the nozzle portion 37 with a piezoelectric element instead of the heater 38.

Hereinafter, the way of applying the sample to the features of the biochip 12 will be described. First, the lid 11 of the body 10 shown in FIG. 1 is opened so as to insert the biochip 12 between the pins 15a to 15c (FIG. 2). After closing the lid 11, the buffer nozzle 31 is aligned above the center of rotation A of the biochip 12 by turning the rotative head 20, whereby the motor 13 is driven to supply the buffer on the rotating biochip 12. Due to the centrifugal force, a sufficient amount of buffer on the center of rotation of the biochip 12 spreads towards the periphery of the biochip 12 to moisten the entire surface of the biochip 12 while an excessive amount of buffer is blown off by the centrifugal force and collected at the bottom of the body 10. In such a manner, the surface of the biochip 12 is evenly covered with a thin layer of buffer.

Then, while rotating the rotative head 20, the sample nozzle 32 is aligned above the center of rotation A of the biochip 12. The sample is injected into the sample injection opening 36 of the sample nozzle 32 shown in FIG. 5 with a micropipette, or the like. The nozzle portion 37 with the narrow aperture is kept full of the sample due to a capillary action. In such a state, a pulsed current is passed to the heater 38 so that a sample drop leaves the tip of the nozzle portion 37 to the center of rotation A of the biochip 12. The sample drop applied to the moistened surface of the biochip 12 spreads toward the periphery of the biochip 12 to cover the entire features due to the centrifugal force generated by the rotating biochip 12.

Figure 6:
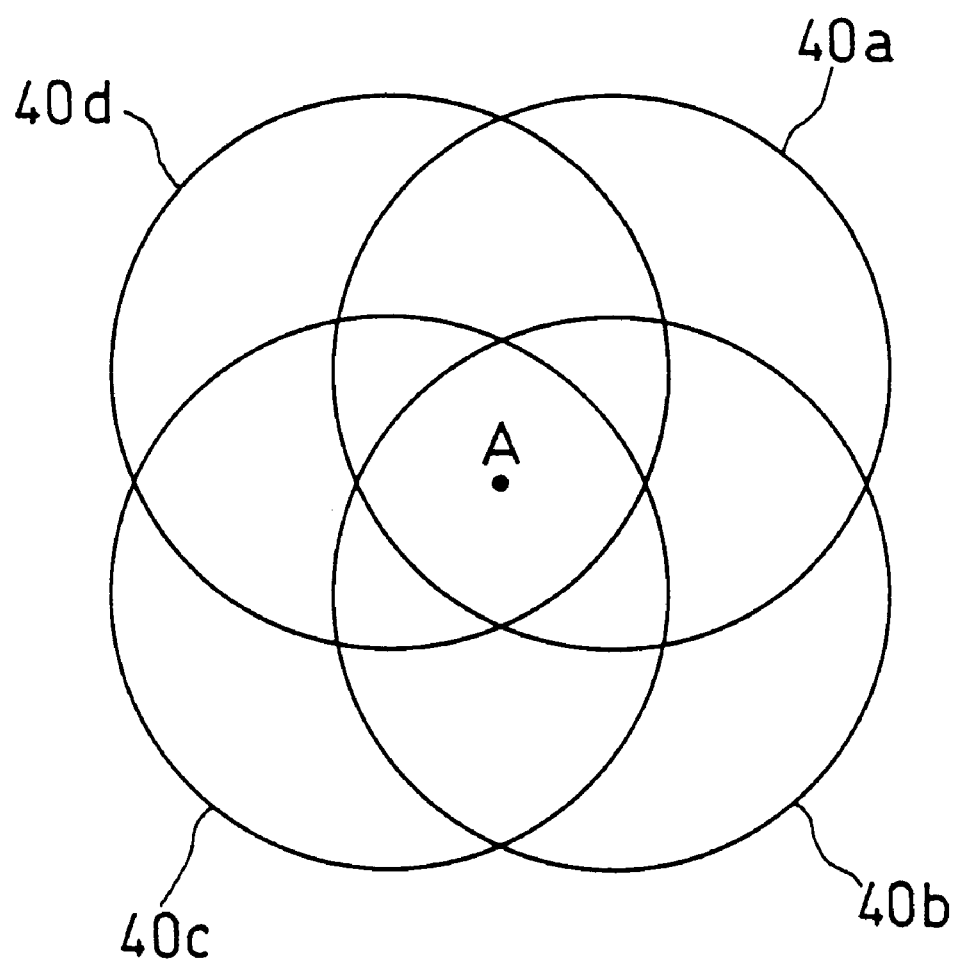
FIG. 6 is a schematic view for explaining positions of sample drops applied on the biochip.

When an amount of a sample drop leaving the sample nozzle 32 is very small and the position of application is shifted from the center of rotation A of the biochip 12, the sample may not be evenly applied to the entire features. In this case, a plurality of sample drops are successively applied to the center of rotation of the biochip 12 rotating at high speed so that the sample can be applied to the entire features over the surface of the biochip 12. Preferably, as schematically shown in FIG. 6, the timings of the pulsed currents passed to the heater 38 are determined in connection with the rotational position of the biochip 12 such that the positions of the successively applied sample drops 40a to 40d are equally dispersed with respect to the center of rotation A.

Figure 7:
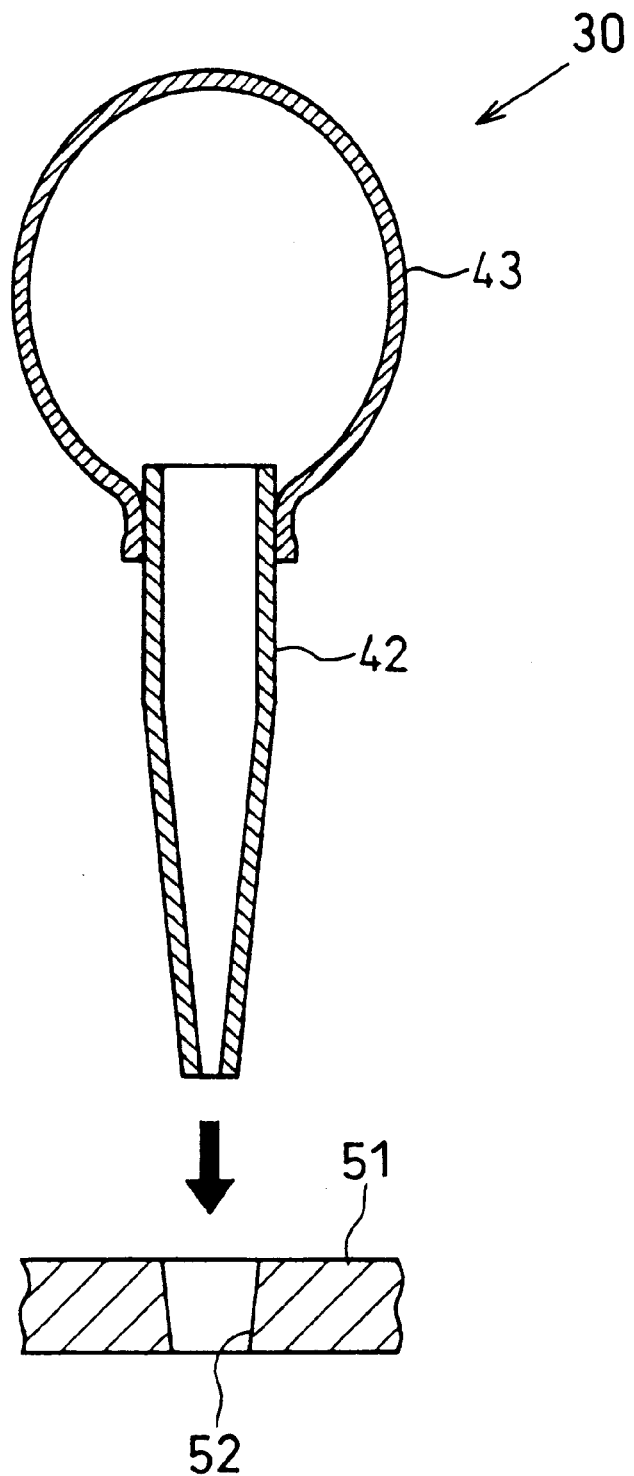
FIG. 7 is a schematic cross-sectional view for illustrating another example of sample nozzle.

FIG. 7 is a schematic cross-sectional view for illustrating another example of sample nozzle 30. In order to receive this sample nozzle 30, a rotative head 51 is provided with a tapered aperture 52 having a diameter decreasing toward the bottom. The sample nozzle 30 is formed using a micropipette 42 or a cylinder. The micro-pipette 42 carrying a sample in a tip thereof is inserted into the tapered aperture 52 of the rotative head 51 such that the tip of the micropipette 42 is fixed therein as supported by the internal wall formed by the tapered aperture 52. By pressing an upper portion 43 of the fixed sample nozzle 30, a sample drop is applied to the center of rotation A of the rotating biochip 12. A minute amount of sample applied from the micropipette 42 to the center of rotation A of the biochip 12 spreads toward the periphery of the biochip 12 due to the centrifugal force and covers the entire features.

Figure 8:
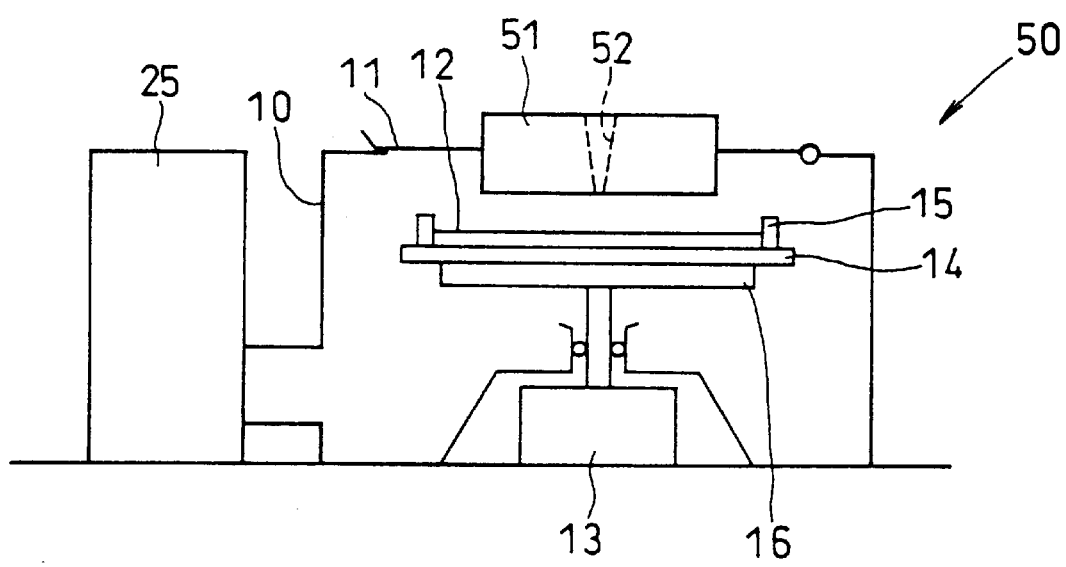
FIG. 8 is a schematic cross-sectional view showing another example of sample application device.

FIG. 8 is a schematic cross-sectional view showing another example of sample application device 50 which has a different head part for injecting a buffer and a sample drop from the sample application device 1 shown in FIG. 1. In FIG. 8, the same reference numerals denote the same components in FIG. 1 and the details thereof are omitted. A lid 11 of a body 10 is provided with the injection head 51 having the tapered aperture 52 above the rotation axis of a motor 13.

As described above with reference to FIG. 7, the tip of the micropipette 42 is inserted into the nozzle-receiving aperture 52. The micropipette 42 in the nozzle-receiving aperture 52 is located immediately above the center of rotation of a biochip 12. Therefore, when a sufficient amount of buffer is dropped from the micropipette 42 to the center of rotation of the rotating biochip 12, it spreads towards the periphery of the biochip 12 to cover the entire surface of the biochip 12. Then, a sample is applied using the micropipette 42 in the same manner. Similarly, the sample applied to the center of rotation of the rotating biochip 12 spreads towards the periphery of the biochip 12 to cover the entire features due to the centrifugal force caused by the rotation.

Figure 9A:
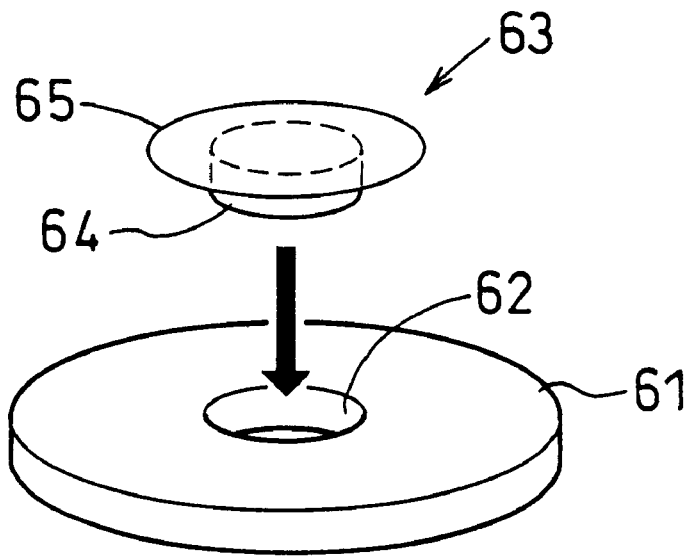
FIGS. 9A and 9B are illustrations for explaining an application of the present invention to another type of biochip having an opening in the center thereof.
Figure 9B:
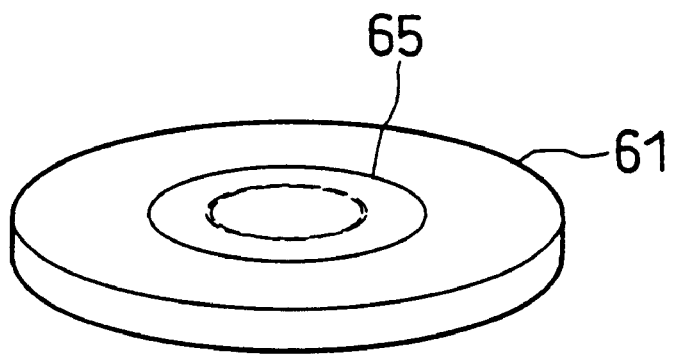
Figure 10:
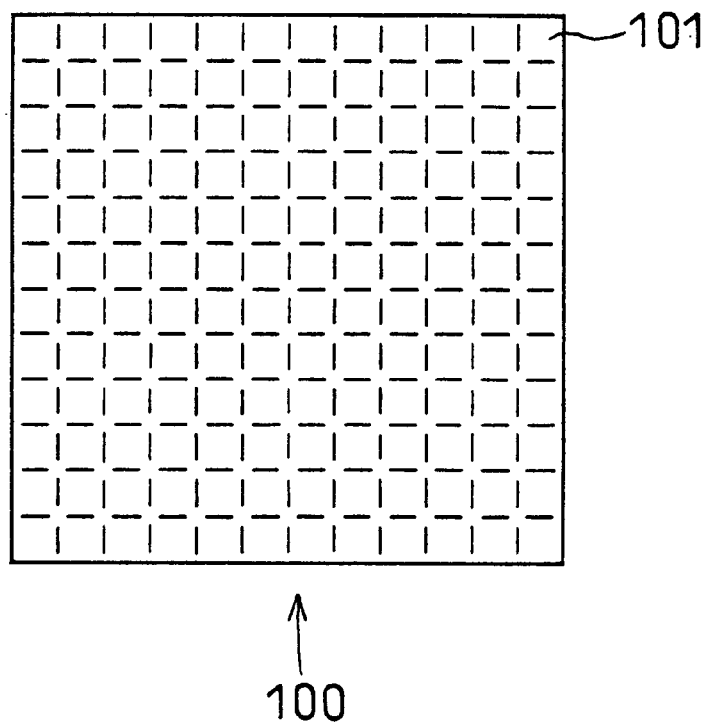
FIG. 10 is a schematic view for explaining a conventional biochip.

FIGS. 9A and 9B are illustrations for explaining an application of the present invention to another type of biochip 61 having an opening 62 in the center thereof. The biochip 61 is not effective in the sample application devices 1 and 50 by itself in supplying a sample over entire features.

As shown in FIG. 9A, a supplementary member 63 is inserted into the opening 62 of the biochip 61. The supplementary member 63 includes a plug portion 64 that fits the opening 62 and a sheet portion 65 that partially covers the upper surface of the biochip 61. The sheet portion 65 has a slightly larger diameter than that of the opening 62 and is composed from glass, polycarbonate, or the like. As shown in FIG. 9B, the biochip 61 with the supplementary member 63 has a flat upper surface of a generally equal height. As a result, the biochip 61 with the supplementary member 63 can be mounted, for example, on the sample application device 1 of the present invention shown in FIG. 1 to apply a sample to entire features as described above.

A temperature controller 16 (FIG. 1) can control the temperature of the biochip 61 in accordance with a pre-programmed temperature cycle. For example, the biochip 61 may be heated to a relatively high temperature before or after applying a sample to the biochip 61 and then gradually cooled down for annealing. Such a temperature control allows hybridization and PCR under optimal conditions.

Hereinafter, an example of conducting PCR utilizing a temperature controller of a sample application device of the invention will be described. PCR allows a specific fragment of DNA to amplify about $10^6$-fold in about 3 hours.

A PCR solution is prepared which has a composition of, for example, in 100 µl, 5 µl template DNA (200 µl/ml), 10 µl buffer solution (500 mM KCl, 100 mM Tris-HCl (pH8.3), 25 mM $MgCl_2$, 0.2% gelatin), 16 µl dNTP mixture (1.2 mM each), 5 µl 2 types of primer (2 µM), 58 µl distilled water and 1 µl Taq polymerase.

This PCR solution is dropped onto and applied to a biochip of the sample application device of the invention before initiating the reaction. Alternatively, a container containing the PCR solution is placed on a rotative plate 14 before initiating the reaction. In this case, the container is made of a heat resistant material and the size thereof is determined such that it can be placed on the rotative plate 14 and such that it can accommodate the PCR solution. Other than that, the container may be of any type. The device is preferably provided with a lid to prevent the PCR solution from evaporating. In the case where there is no lid, the surface of the PCR solution may be covered with mineral oil or liquid paraffin. Alternatively, a PCR disk having a rim for preventing the solution from spilling may be prepared and mounted on the rotative plate 14 to thereby conduct PCR.

PCR is performed as programmed below. First, the template DNA is maintained at 93° C. for 3 minutes to be separated into single-strand DNA which is then synthesized under 20 to 30 cycles of: 93° C. for 1 min.; 55° C. for 1.5 min.; and 7° C. for 1.5 min. These temperatures and periods vary depending on the template DNA used; though in most cases, synthesis takes place under the above conditions. At the end of the above cycles, the DNA is further synthesized at 72° C. for 10 min., and thereafter cooled to 4° C. to terminate the reaction.

According to the present invention, a small amount of sample is efficiently used to evenly cover entire features of a biochip.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

All publications, including patent and patent application cited herein are incorporated herein by reference in their entirety.

What is claimed is:

1. A sample application device comprising:
    a biochip supporting member for supporting a biochip including a plurality of regions bound with various probes;
    a driver for rotating the biochip supporting member; and
    a sample injection member for dropping the sample onto generally a center of rotation of the biochip.

2. A sample application device comprising:
    a biochip supporting member for supporting a biochip including a plurality of regions bound with various probes;
    a driver for rotating the biochip supporting member;
    a buffer injection member for dropping a buffer onto generally a center of rotation of the biochip; and
    a sample injection member for dropping a sample onto generally the center of rotation of the biochip.

3. A sample application device according to either claim 1 or 2, comprising a humidifier for keeping the ambient atmosphere around the biochip at a high humidity; and a temperature controller for controlling the temperature of the biochip.

4. A sample application device according to either claim 1 or 2, wherein the sample injection member is used to apply a plurality of sample drops to generally the center of rotation of the biochip.

* * * * *